(12) United States Patent
Prat et al.

(10) Patent No.: US 8,835,165 B2
(45) Date of Patent: Sep. 16, 2014

(54) SPONTANEOUSLY IMMORTALIZED MULTIPONENT MESENCHYMAL CELL-LINE DERIVED FROM MOUSE SUBCUTANEOUS ADIPOSE TISSUE: TOOL FOR REGENERATIVE MEDICINE AND BIOACTIVE MOLECULES AND/OR DRUGS SCREENING

(75) Inventors: Maria G. Prat, Turin (IT); Stefano Pietronave, Felizzano (IT); Andrea Zamperone, Santhia (IT)

(73) Assignee: Universita Degli Studi del Piemonte Orientale "Armedeo Avogadro", Vercelli (IT)

( * ) Notice: Subject to any disclaimer, the term of this patent is extended or adjusted under 35 U.S.C. 154(b) by 0 days.

(21) Appl. No.: 13/309,132

(22) Filed: Dec. 1, 2011

(65) Prior Publication Data

US 2012/0142002 A1 Jun. 7, 2012

Related U.S. Application Data

(60) Provisional application No. 61/344,973, filed on Dec. 1, 2010.

(51) Int. Cl.
*C12N 5/00* (2006.01)
*C12N 5/02* (2006.01)
*C12N 5/08* (2006.01)
*C12N 5/0775* (2010.01)
*G01N 33/50* (2006.01)

(52) U.S. Cl.
CPC .......... *G01N 33/5073* (2013.01); *C12N 5/0667* (2013.01); *C12N 2503/02* (2013.01)
USPC .......................................... 435/325; 435/372

(58) Field of Classification Search
None
See application file for complete search history.

(56) References Cited

U.S. PATENT DOCUMENTS 6,645,763 B2 * 11/2003 Kobayashi et al. ........... 435/366
2010/0120915 A1 * 5/2010 Beierle ......................... 514/561

* cited by examiner

*Primary Examiner* — Michail Belyavskyi
(74) *Attorney, Agent, or Firm* — Nixon & Vanderhye PC

(57) ABSTRACT

Disclosed is a spontaneously immortalized multipotent mesenchymal cell-line, wherein the cell-line has been isolated from mouse subcutaneous adipose tissue, and wherein the cell-line presents fibroblastoid morphology and expresses Sca-1, c-Kit/CD117, nestin, nucleostemin, CD44 and CD106 markers.

7 Claims, 9 Drawing Sheets
(4 of 9 Drawing Sheet(s) Filed in Color)

SEQUENCE LISTING

```
<160> NUMBER OF SEQ ID NOS: 20

<210> SEQ ID NO 1
<211> LENGTH: 25
<212> TYPE: DNA
<213> ORGANISM: artificial
<220> FEATURE:
<223> OTHER INFORMATION: Sca-1 forward primer

<400> SEQUENCE: 1
actgtgcctg caaccttgtc tgaga                                      25

<210> SEQ ID NO 2
<211> LENGTH: 20
<212> TYPE: DNA
<213> ORGANISM: artificial
<220> FEATURE:
<223> OTHER INFORMATION: Sca-1 reverse primer

<400> SEQUENCE: 2
gtccaggtgc tgcctccatt                                            20

<210> SEQ ID NO 3
<211> LENGTH: 20
<212> TYPE: DNA
<213> ORGANISM: artificial
<220> FEATURE:
<223> OTHER INFORMATION: c-Kit forward primer

<400> SEQUENCE: 3
gccctaatgt cggaactgaa                                            20

<210> SEQ ID NO 4
<211> LENGTH: 20
```

```
<212> TYPE: DNA
<213> ORGANISM: artificial
<220> FEATURE:
<223> OTHER INFORMATION: c-kit reverse primer

<400> SEQUENCE: 4
ttgcggatct cctcttgtct                                             20

<210> SEQ ID NO 5
<211> LENGTH: 19
<212> TYPE: DNA
<213> ORGANISM: artificial
<220> FEATURE:
<223> OTHER INFORMATION: Nucleostemin forward primer

<400> SEQUENCE: 5
gggaaaagca gtgtcatta                                              19

<210> SEQ ID NO 6
<211> LENGTH: 18
<212> TYPE: DNA
<213> ORGANISM: artificial
<220> FEATURE:
<223> OTHER INFORMATION: Nucleostemin reverse primer

<400> SEQUENCE: 6
gggatggcaa tagtaacc                                               18

<210> SEQ ID NO 7
<211> LENGTH: 20
<212> TYPE: DNA
<213> ORGANISM: artificial
<220> FEATURE:
<223> OTHER INFORMATION: islet-1 forward primer

<400> SEQUENCE: 7
gcctcagtcc cagagtcatc                                             20

<210> SEQ ID NO 8
<211> LENGTH: 20
<212> TYPE: DNA
<213> ORGANISM: artificial
<220> FEATURE:
<223> OTHER INFORMATION: islet-1 reverse primer

<400> SEQUENCE: 8
agagcctggt cctccttctg                                             20

<210> SEQ ID NO 9
<211> LENGTH: 21
<212> TYPE: DNA
<213> ORGANISM: artificial
<220> FEATURE:
<223> OTHER INFORMATION: nestina forward primer

<400> SEQUENCE: 9
tcaaggggag gccaggaagg a                                           21

<210> SEQ ID NO 10
<211> LENGTH: 22
<212> TYPE: DNA
<213> ORGANISM: artificial
<220> FEATURE:
<223> OTHER INFORMATION: nestina reverse primer

<400> SEQUENCE: 10
```
ctgcagcccc actcaagcca tc                                            22

<210> SEQ ID NO 11
<211> LENGTH: 18
<212> TYPE: DNA
<213> ORGANISM: artificial
<220> FEATURE:
<223> OTHER INFORMATION: pro-collagen I forward primer

<400> SEQUENCE: 11
gaagtcagct gcatacac                                                 18

<210> SEQ ID NO 12
<211> LENGTH: 18
<212> TYPE: DNA
<213> ORGANISM: artificial
<220> FEATURE:
<223> OTHER INFORMATION: pro-collagen I reverse primer

<400> SEQUENCE: 12
aggaagtcca ggctgtcc                                                 18

<210> SEQ ID NO 13
<211> LENGTH: 21
<212> TYPE: DNA
<213> ORGANISM: artificial
<220> FEATURE:
<223> OTHER INFORMATION: osteocalcin forward primer

<400> SEQUENCE: 13
cctcagtccc cagcccagat c                                             21

<210> SEQ ID NO 14
<211> LENGTH: 21
<212> TYPE: DNA
<213> ORGANISM: artificial
<220> FEATURE:
<223> OTHER INFORMATION: osteocalcin reverse primer

<400> SEQUENCE: 14
cagggcagag agagaggaca g                                             21

<210> SEQ ID NO 15
<211> LENGTH: 21
<212> TYPE: DNA
<213> ORGANISM: artificial
<220> FEATURE:
<223> OTHER INFORMATION: gapdh forward primer

<400> SEQUENCE: 15
atcactgcca cccagaagac t                                             21

<210> SEQ ID NO 16
<211> LENGTH: 21
<212> TYPE: DNA
<213> ORGANISM: artificial
<220> FEATURE:
<223> OTHER INFORMATION: gapdh reverse primer

<400> SEQUENCE: 16
atcgaaggtg gaagagtggg a                                             21

<210> SEQ ID NO 17
<211> LENGTH: 39
<212> TYPE: DNA
<213> ORGANISM: artificial

-continued

```
<220> FEATURE:
<223> OTHER INFORMATION: telomere forward primer

<400> SEQUENCE: 17
cggtttgttt gggtttgggt ttgggtttgg gtttgggtt                              39

<210> SEQ ID NO 18
<211> LENGTH: 39
<212> TYPE: DNA
<213> ORGANISM: artificial
<220> FEATURE:
<223> OTHER INFORMATION: telomere reverse primer

<400> SEQUENCE: 18
ggcttgcctt acccttaccc ttacccttac ccttaccct                              39

<210> SEQ ID NO 19
<211> LENGTH: 21
<212> TYPE: DNA
<213> ORGANISM: artificial
<220> FEATURE:
<223> OTHER INFORMATION: 36B4 forward primer

<400> SEQUENCE: 19
actggtctag gacccgagaa g                                                 21

<210> SEQ ID NO 20
<211> LENGTH: 21
<212> TYPE: DNA
<213> ORGANISM: artificial
<220> FEATURE:
<223> OTHER INFORMATION: 36B4 reverse primer

<400> SEQUENCE: 20
tcaatggtgc ctctggagat t                                                 21
```

SPONTANEOUSLY IMMORTALIZED MULTIPONENT MESENCHYMAL CELL-LINE DERIVED FROM MOUSE SUBCUTANEOUS ADIPOSE TISSUE: TOOL FOR REGENERATIVE MEDICINE AND BIOACTIVE MOLECULES AND/OR DRUGS SCREENING

This application claims priority from U.S. Provisional Application No. 61/344,973, filed Dec. 1, 2010, the entire content of which is incorporated herein by reference.

FIELD OF THE INVENTION

The instant description concerns a spontaneously immortalized multipotent mesenchymal cell-line derived from mouse subcutaneous adipose tissue and its uses as tool for regenerative medicine and bioactive molecules and/or drugs screening.

BACKGROUND

Regenerative Medicine is a relatively young interdisciplinary science intended to the ex vivo manufacture of 3D proto-tissues able to replace injured organs and solid tissues requiring the strict cooperation of material scientists, who should fabricate biocompatible scaffolds with a wide range of physical parameters, biochemists and molecular biologists, who should produce highly purified, bioactive molecules in large quantities and cell biologists, who should provide the appropriate cells.

Adult STEM cells, and in particular mesenchymal stem cells, are so far the best cell type for this purpose, because of their properties of self-renewal and multipotency. They were originally isolated from bone marrow; more recently subcutaneous adipose tissue was also shown to contain adult stem cells in its stromal component and it is receiving more and more attention due to the simple surgical procedure, the easy and repeatable access, the easy enzyme-based isolation procedures and the relative large available quantities.

Adipose-derived Stem Cells (ADS) display morphological, immune phenotypic, colony frequency, and differentiation capacity similar to those of the longer-time characterized mesenchymal stem cells isolated from bone marrow. As an example, they can be easily induced to differentiate towards osteoblasts, adipocytes, chondrocytes.

In regenerative medicine applied to the ex vivo generation of solid tissues, the microenvironment where cells are inserted plays an essential role contributing physical—e.g. mechanical, topographical, electric-cues, as well as chemical signals—e.g. growth or differentiation/factors, adhesion molecules.

The great efforts to develop new materials and innovative cell culture systems are often hampered by the relatively limited in vitro growth of the cells, since in these complex systems primary cells are generally used, which inevitably undergo senescence within few passages.

Fresh primary stem cells must thus be continuously isolated, which is time-consuming and requires killing of animals.

Therefore, the establishment of a cell line with features of stem/progenitor cells may help to overcome the limitations identified above. Moreover, continuous cell lines may provide a more homogeneous and reproducible reagent for cell cultures.

SUMMARY OF THE INVENTION

Taking into consideration these premises, it is therefore felt the need for immortalized multipotent mesenchymal cell-lines.

According to the invention, the above object is achieved thanks to the solution as called for in the claims that follow, which are an integral part of the disclosure of the invention as provided herein. An embodiment of the present invention concerns a spontaneously immortalized multipotent mesenchymal cell-line, wherein the cell-line has been isolated from mouse subcutaneous adipose tissue, and wherein the cell-line presents fibroblastoid morphology and expresses Sca-1, c-Kit/CD117, nestin, nucleostemin, CD44 and CD106 markers; the cell line being the cell-line designated as m17.ASC has been deposited with Advanced Biotechnology Center (Genoa, Italy) under the terms of the Budapest Treaty on Nov. 10, 2010 and assigned accession number ICLC PD No. 10001.

The present description specifically concerns the generation, characterization and use of the clone m17.ASC, which spontaneously immortalized from the stromal fraction of adipose tissue of a fvb mouse. These cells maintained a normal karyotype and stem phenotype for more than 120 generations, could be induced to differentiation towards osteogenic, chondrogenic, adipogenic and cardiogenic phenotypes. These cells did not display in vitro transforming activity or in vivo tumorigenicity. When GFP transduced m17.ASCs were injected in the portal vein or in the spleen of syngeneic monocrotaline and cyclophosphamide treated mice, they were able to engraft in the liver.

On the basis of its features the continuous stem cell line m17.ASC thus offers a valid tool to set up experimental conditions as in the case of a bio-mimetic approach, where researchers try to recreate in vitro specific aspects of the in vivo environment, by combining different technologies such as 3-dimensional structures, biochemical cues (selected growth factors and hormones) and physical forces (electrical, mechanical and topographical) and thereby instruct the cells to assemble into functional tissues.

Moreover the continuous stem cell line m17.ASC can be advantageously used in screening compounds to test their ability in inducing or inhibiting proliferation and/or differentiation in tissue-specific phenotype.

In a further embodiment, the instant description concerns a method of testing the ability of an agent, compound or factor to modulate the tissue-specific differentiation of an uncommitted cell which comprises:
  culturing the spontaneously immortalized multipotent mesenchymal cell-line m17.ASC in a growth medium which maintains the spontaneously immortalized multipotent mesenchymal cell-line as lineage uncommitted cells;
  adding the agent, compound or factor under test; and
  determining the tissue phenotype of the so contacted cells by mRNA expression, antigen expression or other means.

In a further embodiment, the instant description concerns a method of testing the ability of an agent, compound or factor to inhibit the tissue-specific differentiation of an uncommitted cell which comprises:
  culturing the spontaneously immortalized multipotent mesenchymal cell-line m17.ASC in a growth medium in presence of a tissue-specific differentiation factor;
  adding the agent, compound or factor under test; and determining if the so contacted cells did not acquire the tissue-specific phenotype by mRNA expression, antigen expression or other means.

In a further embodiment, the instant description concerns a method of testing the ability of an agent, compound or factor to modulate the proliferation of an uncommitted cell which comprises:

culturing the spontaneously immortalized multipotent mesenchymal cell-line m17.ASC in a growth medium which maintains the spontaneously immortalized multipotent mesenchymal cell-line as uncommitted cells;

adding the agent, compound or factor under test; and determining the proliferation and tissue phenotype of the so contacted cells by mRNA expression, antigen expression or other means.

In a further embodiment, the instant description concerns a method of testing the biocompatibility of a scaffold for cell adhesion and proliferation which comprises:

culturing the spontaneously immortalized multipotent mesenchymal cell-line m17.ASC on the scaffold in presence of a culture medium;

determining the cell proliferation by cell counting.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
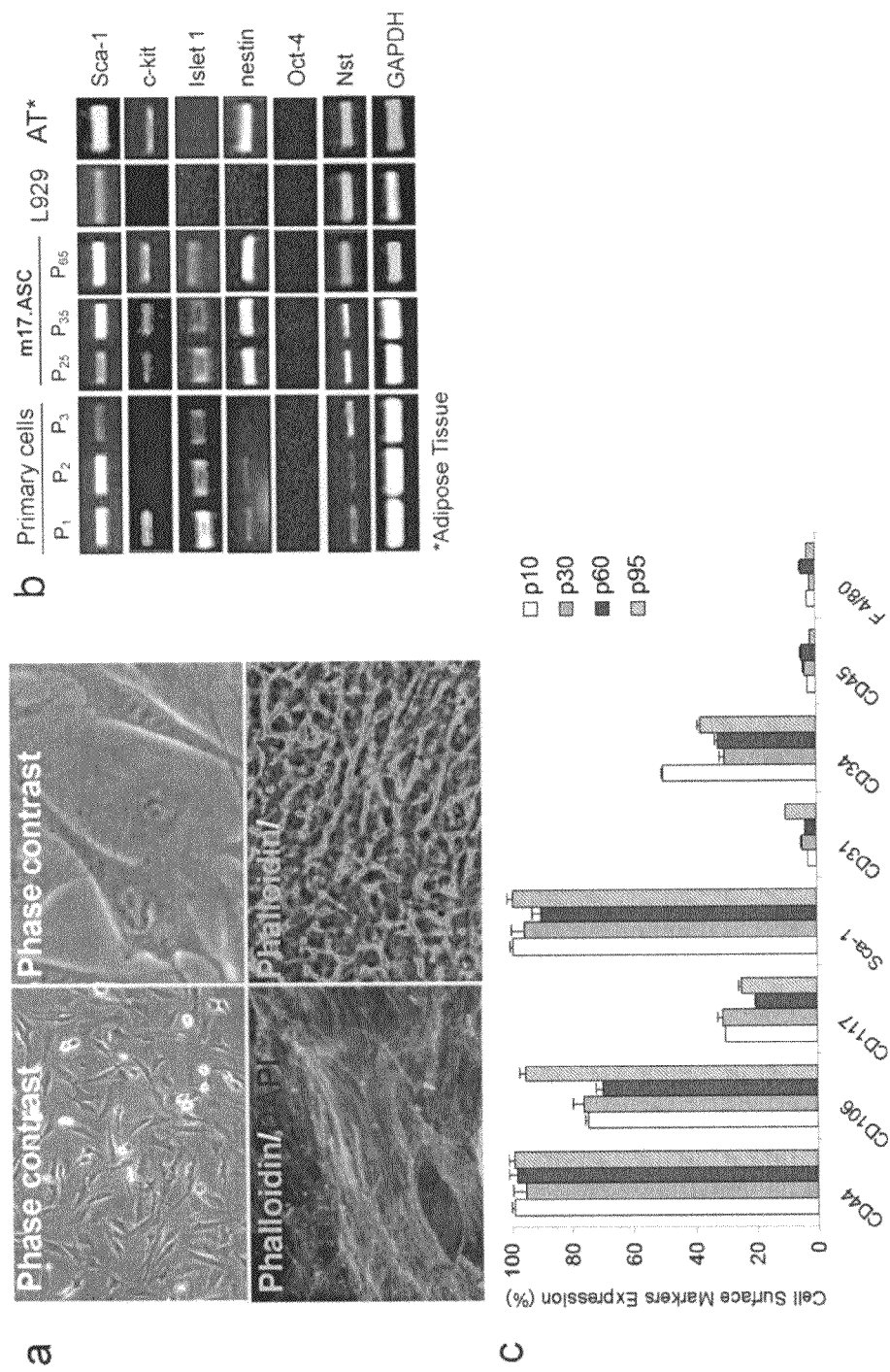
FIGS. 1a-1c: Properties of the clonal cell line m17.ASC. Morphology of the m17.ASC clone, which was generated from Sca-1$^{POS}$ cell cultures plated at low density (200 cells/cm$^2$) at the phase contrast microscope at two different enlargment (FIG. 1a, top) or after staining with phallodin-TRITC and DAPI or Sca-1 (FIG. 1a, bottom). Immunophenotype of m17.ASCs, characterized in RT-PCR (FIG. 1b) and cytofluorimetry (FIG. 1c) for different sternness markers at different passages. The clone has a fibroblast-like aspect and continues to express sternness markers with time. Representative experiments out of the three performed are reported.

Adult stem cells are a key component for regenerative medicine applied to solid tissues and organs, the other two being biocompatible, possibly bioresorbable, scaffolds and soluble growth factors supporting cell growth and differentiation.

By definition stem cells are endowed of multipotency, which can be unlocked and guided towards specific histotypes by the physical and chemical cues provided by the environment in which they are kept ex vivo.

The aim of researchers involved in regenerative medicine is thus to recreate the right environment, mimicking as much as possible the in vivo situation of a living organism, where tissues are formed and renewed under the influence of orchestrated spatial and temporal regulated physical and chemical stimuli.

In vitro tissue engineering is a relatively young discipline, and, although great advances have been made, many investigations are going on to refine and ameliorate these complex biomimetic constructs.

Many materials are being developed for scaffolds, which cannot be a mere substrate, but must be able to release mechanical and structural signals, and thus are different depending on the properties of the tissues to be engineered. As an example, the role of the scaffold design is particularly evident when stem/progenitor cells are used to fabricate architecturally complex engineered tissues, such as the myocardium.

It is thus clear the advantage of having a standardized and easily available cell source. The same is true for the biochemical component, where growth factors and cytokines at the right concentration and combination must be used.

Herein the properties, as well as some of the possible applications, of a cell line stabilized from a clone of spontaneously immortalized murine adult mesenchymal stem cells are described.

The m17.ASCs originated from cultures in which cells from the vascular stromal fraction of adipose tissue, selected for the expression of the sternness marker Sca-1, were plated at low concentrations. The clone has now been propagated for more than two years with no changes in its morphology, sternness markers, duplication time, multipotency and stable telomere length. It displays a normal karyotype and has not in vitro transforming activity, nor in vivo tumorigenic activity. When cells were transplanted in the liver and the spleen of syngeneic mice, they efficiently engrafted.

m17.ASC displays the typical fibroblastoid morphology and expresses the well acknowledged sternness markers Sca-1, c-Kit/CD117, nestin, nucleostemin, CD44, CD106, with the exception of Oct-4. Moreover, as reported also by some other groups, it expresses a certain level of CD34, a widely used marker of hematopoietic stem and progenitor cells, also highly expressed in vascular endothelial cells and their precursors (Asahara et al., 1997).

The clone displayed multipotency, since it differentiated towards adipogenic, chondrogenic, osteogenic, and cardiogenic phenotypes, upon appropriate stimulation with media containing specific differentiation factors and molecules or in co-culture conditions. In particular, when cultured in presence of dexamethasone, indometacin, insulin, 3-isobutyl-1-methilxantin, they were driven to adipocytes; when cultured in presence of ascorbic acid, $\beta$-glicerophosphate, dexamethasone, they were driven to osteoblastic phenotype and when cultured in sodium piruvate, 2-phospho ascorbate, dexamethasone, TGF$\beta$3, they were driven to chondrogenic phenotype.

These cells could thus be used as a platform to investigate the effect of other new biomolecules or possible combinations or timing and to test the effects of drugs in interfering with the induction of these phenotypes.

The cells of m17.ASC clone could be induced to osteoblastic differentiation also when plated on titanium scaffolds, demonstrating that they are suitable to test unconventional cell culture substrates for tissue engineering.

The fact that the clone emerged as a spontaneously immortalized cell line is noteworthy. Indeed stem cells from murine adipose tissue, as well as from bone marrow, undergo senescence within few passages. To overcome this limitation, cells from the bone marrow were artificially immortalized upon transduction with a vector for mTERT cDNA. However, these cells acquired also transformed and tumorigenic activities, when inoculated in syngeneic recipient animals. By contrast m17.ASCs behave as normal, as evidenced by their inability to proliferate in anchorage-independent conditions or as tumor in syngeneic mice. Karyotype analysis confirmed the normality, since no chromosome number and pattern alterations were found.

The proliferation ability of m17.ASC are strictly dependent on the regulation of telomere length. Since the primary cells progressively reduce their replicative potential and senesce after 7-9 passages, a stabilization of telomere in m17.ASC is expected to occur. The analysis of T/S allow the simultaneous correlation of telomere dynamics within the cell line throughout the different time points and the reference primary cell line at early replication stage.

The m17.ASC cell line is able to maintain a stable proliferative ability and a corresponding substantial telomere stability ($p>0.1$). This data indicate that these cells assumed an immortal phenotype consequent to a clonal selection, where the mechanisms that sustain the proliferation potential are active although the cells do not show a tumoral behaviour.

Due to the many properties of m17.ASC, namely, pluripotency, stability, reproducibility, availability, non transforming or tumorigenic characteristics, ability to engraft in syngeneic mice, this cell model represents a valuable tool for a number of application in ex vivo tissue engineering, in its two main aspects concerning physical (e.g. electrical, mechanical, topographical) or biochemical (selected growth factors, hormones and other biologically active molecules and possibly inhibiting drugs) simulations with the additional advantage that it does not require repeated animal sacrifice. The fact that these cells can engraft in syngeneic mice opens to the possibility to translate some experiments from the in vitro/ex vivo to the in vivo conditions.

m17.ASC cell-line can, thus, be employed for: screening the ability of a compound -easily determinable by an expert of the art- to induce or inhibit differentiation of said cell-line in a tissue-specific phenotype;

screening the biocompatibility of a scaffold —easily determinable by an expert of the art—for adhesion, proliferation and/or differentiation towards a specific phenotype, wherein the specific phenotype is obtained by culturing on that scaffold the m17.ASC cell-line in presence of at least one specific phenotype differentiation compound;

testing the ability of an agent, compound or factor to modulate the tissue-specific differentiation of an uncommitted cell-line which comprises:

culturing the m17.ASC cell-line in a growth medium -easily determinable by an expert of the art- which maintains the m17.ASC cell-line as lineage uncommitted cells;

adding the agent, compound or factor under test; and determining the tissue phenotype of the so contacted m17.ASC cells by mRNA expression, antigen expression or other means—easily determinable by an expert of the art—;

testing the ability of an agent, compound or factor to inhibit the tissue-specific differentiation of an uncommitted cell which comprises:

culturing the m17.ASC cell-line in a growth medium in the presence of a tissue-specific differentiation factor;

adding the agent, compound or factor under test -easily determinable by an expert of the art-; and determining if the so contacted m17.ASC cells do not acquire the tissue-specific phenotype by mRNA expression, antigen expression or other means;

screening agents, compounds or factors for the ability to modulate the tissue-specific differentiation of an uncommitted cell-line, comprising:
culturing the m17.ASC cell-line in a growth medium which maintains the m17.ASC cell-line as lineage uncommitted cells,
adding the agent, compound or factor under test; and
determining the tissue phenotype of the so contacted m17.ASC cells by mRNA expression, antigen expression or other means;

screening agents, compounds or factors for the ability to inhibit the tissue-specific differentiation of an uncommitted cell-line, comprising:
culturing the m17.ASC cell-line in a growth medium in the presence of a tissue-specific differentiation factor,
adding the agent, compound or factor under test; and
determining if the so contacted m17.ASC cells do not acquire the tissue-specific phenotype by mRNA expression, antigen expression or other means;

testing the ability of an agent, compound or factor to modulate the proliferation of an uncommitted cell which comprises:
culturing the m17.ASC cell-line in a growth medium which maintains the m17.ASC cell-line as lineage uncommitted cells;
adding the agent, compound or factor under test; and
determining the proliferation and optionally the tissue phenotype of the so contacted m17.ASC cells by mRNA expression, antigen expression or other means.

Other means for determining the tissue phenotype acquired by the cell-line can be, for example, morphological analysis, biochemical analysis, microarray analysis, electrophysiological recordings.

The m17.ASC line can, thus, be employed to screen any culture medium supposed to be able to maintain its stemness properties. As an example, these cells could be expanded in Dulbecco's modified Eagle medium (Lonza-Basel, CH), 10% Fetal Bovine Serum (Lonza), 50 IU/ml penicillin and 50 µg/ml streptomycin, insulin-transferrin-selenium 1× (Invitrogen SRL, S. Giuliano Milanese, Italy), 300 ng/ml retinoic acid, 0.8 µg/ml linoleic acid, 2 mM L-glutamine, 0.1 ng/ml insulin-like growth factor 1, and 0.1 ng/ml endothelial growth factor. Their stemness status could be constantly monitored on the basis of their immunophenotype profile (expression of Sca-1, c-kit, CD44, CD106 markers detectable both in PCR and in immunofluorescence with specific antibodies) and their multilineage differentiation ability, upon appropriate stimulation.

Similarly, m17.ASC cell-line can be employed to screen any putative potential differentiation factor or cytokine or microRNA—easily determinable by an expert of the art—especially if the latter are presumed to induce differentiation towards the chondrogenic, the osteogenic, the adipogenic or the cardiogenic phenotypes. As an example, these cells could be induced to the osteogenic differentiation by culturing with 50 µg/ml ascorbic acid, 10 mM β-glicerophosphate, 10 nM dexamethasone and differentiation could be monitored by the expression of the marker osteocalcin in PCR or by staining with alizarin red or calcein.

The m17.ASC line can be employed to screen the biocompatibility of a scaffold -easily determinable by an expert of the art- for adhesion, proliferation and/or differentiation towards a specific phenotype. As an example a scaffold in titanium could be suitable in the case of osteogenic differentiation, which could be monitored as described above.

The m17.ASC line can be employed to screen for inhibitors of proliferation or differentiation. As an example the p38 inhibitor SB203580 was able to inhibit the proliferation induced by Hepatocyte Growth Factor in mouse mesenchymal stem cells from bone (Forte G, et al.).

Certain aspects of the invention are described in greater detail in the Example that follows.

EXAMPLE

Materials and Methods
Cell isolation, Cloning, Culturing and Transduction

The Stromal Vascular Fraction (SVF) was isolated from minced s.c. and epididymal/parametrial fat pads of 12-week-old mice (fvb strain, purchased by Charles River, Calco, Italy) by digestion with 0.1% type I collagenase (Worthington Biochemical, Lakewood, N.Y.) in PBS at 37° C. for 1 h. After filtration through 30-µm nylon filters (Miltenyi Biotec GmbH, Bergisch Gladbach, Germany) and centrifugation for 1 min at 400 ×g, floating adipocytes were removed, the pellet (SVF) was treated with erythrocyte lysis buffer (154 mM NH 4 Cl, 20 mM Tris pH7.5), sorted by immunomagnetic procedure with Sca-1 mouse-specific antibodies (Miltenyi Biotec) and plated ($10 \times 10^4$ cells/cm$^2$) in Dulbecco's modified Eagle medium (Lonza-Basel, CH), 10% Fetal Bovine Serum (Lonza), 50 IU/ml penicillin and 50 pg/ml streptomycin, insulin-transferrin-selenium 1× (Invitrogen SRL, S. Giuliano Milanese, Italy), 300 ng/ml retinoic acid, 0.8 µg/ml linoleic acid, 2mM L-glutamine, 0.1 ng/ml insulin-like growth factor 1, and 0.1 ng/ml endothelial growth factor (hereafter referred to as "expansion medium"). Cells were maintained at 37° C., in the presence of 5% $CO_2$ and regularly passaged when 90% confluent at a ratio 1/3, with changes in medium every 2-3 days. After the second passage some cells were plated at low density (200 cells/ cm$^2$). The m17.ASC clone was detectable after 1 week, grown and recloned. This cell line can be passaged 1/8-1/10 every 3 days. Cell doubling as well as telomeres length was evaluated in a 32 days time span. m17.ASC were sequentially passaged every three days at a starting density of $1 \times 10^5$/cm$^2$. In parallel the same procedure was pursued for freshly isolated primary cells at p1, which were used as reference. Cells were transduced with a Lentiviral Vector (LV) for the expression of Green Fluorescent Protein (GFP) under the control of an ubiquitous promoter (PGK), as described (Merlin et al., 2009). NIH-3T3, NIH-3T3-MET-EC- (Merlin et al., 2009) and MC3T3, an osteoblast line, and L929, a fibroblast line, both purchased from the American Type Cell Collection, were used as controls.

All procedures were carried out in accordance with the European Community Directive for Care and Italian Laws on animal experimentation (Law by Decree 116/92).

Immunofluorescence Experiments

Cells were washed in PBS, fixed in 4% PAF for 20 minutes, washed again, incubated with anti-Sca-1 antibody PE-conjugated (BD Biosciences, Buccinasco, Italy) or rabbit-anti-Connexin 43, anti-GATA-4, anti-MEF2c (Abcam, Cambridge, UK) 1 hour at room temperature (antibody was diluted in TBS with 4% FBS), followed by secondary goat-anti-rabbit-IgG-FITC-labelled antibodies (Biolegend, San Diego, Calif., USA). Fixed cells were permeabilized in 0.2% Triton ×100 in PBS, washed and incubated with phalloidin-FITC (Sigma-Aldrich, St. Louis, Mo., 1:500) or monoclonal antibodies anti-Troponin T, anti-alpha-sarcomeric actinin (Abcam), followed by secondary goat-anti-mouse IgG-TRITC-labeled antibodies (Biolegend). Cells were also stained with DAPI (Sigma-Aldrich, 1:200) and after further washes observed at a microscope for fluorescence. For cells in osteogenic differentiation on titanium matrices, cells were labelled with phalloidin-TRITC (Sigma-Aldrich; 1:500) and calcein-FITC (Sigma-Aldrich; 1 mg/ml).

Cytofluorimetric Analysis

Cells were incubated for 20 min with anti-Sca-1-FITC (BD Biosciences) or PE labelled or anti-c-kit-PE (anti-CD117) (Biolegend) and washed twice with ice-cold PBS. Alternatively, cells were stained for 20 min with anti-CD44, CD106, CD-31, CD34, CD45, F480-FITC-labelled antibodies (Biolegend). Cells were then fixed in buffered 1% paraformaldehyde (PFA), 2% FBS for 15 min at 4° C. and were analyzed in a FACScalibur flow cytometer (BD Biosciences) within 48 h.

RT-PCR Analysis

Total RNA was extracted in Trizol® reagent (Invitrogen); 1 µg of RNA was retrotranscribed in cDNA with the RevertAid™ H Minus First Strand cDNA Synthesis Kit (Fermentas, St. Leon-Rot, Germany). PCR reactions were performed using the PCR Master Mix 2× kit (Fermentas) in a final volume of 25 µl containing 50 ng cDNA and 200 nmol/l of each primer. PCR conditions were the following: 94° C. 2', 35 cycles 94° C. 30"-72° C. 30"-72° C. 7'. Only 20 cycles were performed for GAPDH. The primers used for the DNA amplification of the different target genes are listed in Table 1.

ack, 2006). Telomere assay was performed in triplicate with 12.5 µl EVA Green SMX (BioRad), 250 nM of each primer, 35 ng genomic DNA in a 25-µl reaction in a CFX96 thermocycler (BioRad). Results were analyzed with BioRad CFX Manager and exported to Excel (Microsoft, Redmond, Wash.) spreadsheet for analysis. For each data point T/S value was calculated. Shortly, threshold cycle values (Ct) were determined from semilog amplification plots (log increase in fluorescence versus cycle number) for telomere (T) and 36B4 gene (S). The relative ratio of telomere repeat copy number to the 36B4 single copy gene copy number (T/S ratio) for each time point was calculated as $[2^{Ct(telomeres)}/2^{Ct(36B4)}]^{-1}=2^{-\Delta Ct}$, and related to the primary cell line telomere T/S at passage 3 by using the formula $2^{-(\Delta Ctm17.1-\Delta Ctprimary}=2^{-\Delta\Delta Ct}$ (FIG. 5c p>0.1). Samples with a T/S >1.0 have an average telomere length ratio (ATLR) greater than that the primary cell line.

Differentiation Protocols

Cells were plated onto 35 mm dishes ($2\times10^4$ cells/cm$^2$) and cultured in adipogenic medium (Cambrex Biosciences Inc., Verviers, Belgium), consisting of DMEM, 10% FBS, 1 µM dexamethasone, 0.2 mM indometacin, 10 µg/ml insulin, 0.5 mM 3-isobutyl-1-methilxantin) or osteogenic medium (DMEM, FBS 10%, 50 µg/ml ascorbic acid, 10 mM β-glicerophosphate, 10 nM dexamethasone) which was

TABLE 1

| Target gene | forward sequence | Reverse sequence |
|---|---|---|
| Sca-1 | 5'-ACTGTGCCTGCAACCTTGTCTGAGA-3' (SEQ ID No.: 1) | 5'-GTCCAGGTGCTGCCTCCATT-3' (SEQ ID No.: 2) |
| c-kit | 5'-GCCCTAATGTCGGAACTGAA-3' (SEQ ID No.: 3) | 5'-TTGCGGATCTCCTCTTGTCT-3' (SEQ ID No.: 4) |
| Nucleostemin | 5'-GGGAAAAGCAGTGTCATTA-3' (SEQ ID No.: 5) | 5'-GGGATGGCAATAGTAACC-3' (SEQ ID No.: 6) |
| Islet-1 | 5'-GCCTCAGTCCCAGAGTCATC-3' (SEQ ID No.: 7) | 5'-AGAGCCTGGTCCTCCTTCTG-3' (SEQ ID No.: 8) |
| Nestina | 5'-TCAAGGGGAGGCCAGGAAGGA-3' (SEQ ID No.: 9) | 5'-CTGCAGCCCCACTCAAGCCATC-3' (SEQ ID No.: 10) |
| Pro-collagen I | 5'-GAAGTCAGCTGCATACAC-3' (SEQ ID No.: 11) | 5'-AGGAAGTCCAGGCTGTCC-3' (SEQ ID No.: 12) |
| Osteocalcin | 5'-CCTCAGTCCCCAGCCCAGATC-3' (SEQ ID No.: 13) | 5'-CAGGGCAGAGAGAGAGGACAG-3' (SEQ ID No.: 14) |
| GAPDH | 5'-ATCACTGCCACCCAGAAGACT-3' (SEQ ID No.: 15) | 5'-ATCGAAGGTGGAAGAGTGGGGA-3' (SEQ ID No.: 16) |
| Telomere | 5'-CGGTTTGTTTGGGTTTGGGTTTGGGTTT GGGTTTGGGTT-3' (SEQ ID No.: 17) | 5'-GGCTTGCCTTACCCTTACCCTTACC CTTACCCTTACCCT-3' (SEQ ID No.: 18) |
| 36B4 | 5'-ACTGGTCTAGGACCCGAGAAG-3' (SEQ ID No.: 19) | 5'-TCAATGGTGCCTCTGGAGATT-3' (SEQ ID No.: 20) |

The amplified products were resolved by 2% agarose gel electrophoresis, stained with ethidium bromide and documented with GelDoc system (Biorad Laboratories, Milan, Italy). Amplified products match the expected molecular weight.

For telomere length evaluation genomic DNA was extracted from mouse cell lines with Gres whole blood DNA extraction kit (InCura, Cremona, Italy). Real-time PCR was used to assess average telomere length ratio. Telomeric DNA amount was normalized on the quantity of the single-copy gene, the acidic ribosomal phosphoprotein PO (36B4) gene, as previously described (Cawthon, 2002, Callicott and Womchanged every 3 days. After 14 days, cells were washed in cold PBS, fixed with 4% PFA in PBS and stained with Adipored (Cambrex Biosciences) or 40 mM Alizarin Red S, pH 4.1 (Yamakawa et al., 2003). The presence of lipid vacuoles was visualized under fluorescence microscope, while the production of calcium deposits was examined in light microscopy. For chondrogenic differentiation cells ($2.5\times10^5$) were cultured as "pellet" for 30-40 days in 15 ml centrifuge tubes in Chondrogenic Differentiation Medium (Cambrex Biosciences, consisting of DMEM, 100 µg/ml sodium piruvate, 10 ng/ml TGFβ3, 100 nM dexamethasone, 25 µg/ml 2-phospho ascorbate) (Lee et al., 2004). Medium was changed every second day. Cells were then washed, fixed in 4% PAF for 20 min at 4°, included in optimal cutting temperature (OCT) medium (Fisher, Hampton, N.H.) and frozen at −80° C. Five μm sections were cut, fixed again as before, washed, stained with 1% Alcian Blue in 3% acetic acid, pH 2.5 for 30 min and observed at the light microscope.

For cardiomiogenic differentiation two conditions were applied:
 i) cells were plated on fibronectin-coated coverslips and cultured in a commercially available cardiomyocyte differentiation medium (Millipore, Temecula, Calif., USA) for 2-3 weeks following the Company's instructions. Cells were then fixed as above and processed for immunofluorescence with anti-connexin 43 and anti-Troponin T antibodies, followed by appropriate FITC- and TRITC-labelled secondary antibodies and DAPI.
 ii) m17.ASC were co-cultured with neonatal cardiomyocytes (nCMs) isolated from hearts of 1-3-day-old fvb mice, as in the manufacturer's instructions (kit by Worthington Biochemical Corp). Briefly, immediately after isolation, cells were pre-plated for 2 h 30 min to recover the non-adherent-enriched fraction of nCMs, which were then seeded on fibronectin (2 μg/mL), laminin (0.2%), gelatin (0.02%, Sigma-Aldrich) pre-coated glass chamber slides (BD Biosciences). m17.ASC, labeled with DIIC12(3) fluorescent dye (BD Biosciences), were seeded directly onto neonatal cardiomyocytes (1:10 ratio) in complete medium and co-cultures were prolonged up to 7 days. m17.ASC and nCMs alone were used as negative controls. Co-cultures were also carried on with cells isolated from the Stromal Vascular Fraction (SVF) at their second passage and neonatal cardiomyocytes.

Karyotype Analysis

Chromosomal analysis of m17.ASCs was carried out starting from passage 10, and then every 10 passages up to passage 73, using standard G banding method (Seabright, 1971). Briefly, colchicine (10 μg/ml final concentration) was added to 60% confluent cells at 37° C. for one hour. Cells were then detached, centrifuged and pellet was resuspended in hypotonic solution (0.075 M potassium chloride) at 37° C. for 30 minutes. Cells were fixed with Carnoy-fixative solution (methanol/glacial acetic acid 3:1) and dripped on clean slides, which, after some days were immersed in 60° C. solution 1×SCC (sodium chloride and sodium citrate) for 30 minutes, washed with running water, and stained with 0.06% Wright's, pH 6.8, for 10 minutes, rinsed and dried. Unmounted slides were examined using Nikon Eclipse 1000 light microscopy and photographed with Genicon (San Diego, Calif.) software. Thirty high-quality G-banded metaphases were selected each time. The chromosomes were classified according to the International System for Cytogenetic Nomenclature (ISCN, Mitelman, 1995).

Analysis for Anchorage-independent Proliferation

Cells ($5\times10^3$/well) were seeded in 12-well plates in semi-solid medium (0.3% agar -Agar Noble, Sigma- in DMEM 2% FCS). NIH-3T3 cells and NIH-3T3-Met$^{EC-}$ cells (Merlin et al., 2009) were used as negative and positive controls. Medium was replaced weekly; after 3 weeks colonies were stained with MTT [3-(4,5-dimethylthiazol-2-yl)-2,5-diphenyl tetrazolium bromide; Sigma-Aldrich], photographed with versadoc imager and counted with Quantity One colony counting software (Biorad).

Experiments of Cell Proliferation and Differentiation on Titanium Matrices m17.ASCs (about $8\times10^3$) were seeded on titanium grade 2 disks in 50 μl medium for 3 hours before adding the appropriate medium volume. For proliferation and viability assays cells were detached at sequential times (1, 2, 5 days) and counted in an inverted microscope, after being resuspended in a Trypan blue solution. MTT assay was performed on identical samples by adding 100 μl/ml of a 0.5 mg/ml MTT solution in PBS for 4 hours. Samples were then washed, 100 μl DMSO was added, and sample adsorbance was read at 520 nm at the Microplate Reader (Model 3550, Bio-Rad). Three experiments were performed in triplicates. For test Cells plated three days before were used for experiments of osteogenic differentiation with the protocol described above.

In Vivo Transplantation Experiments

Six-seven week old fvb female mice were pretreated with monocrotalin (200 mg/Kg, i.p. injection), a liver endothelium cytotoxic drug, and cyclophosphamide (20 mg/Kg twice a week) and next day they received $1\times10^6$ GFP-m17.ASCs by i.v. injection though the portal vein or $2\times10^6$ GFP-m17.ASC by intrasplenic injection (Follenzi et al., 2008). Mice were observed daily and at different time points after the m17.ASCs injection they were killed (3 h, 72 h, 1 week). Livers were fixed in 4% PAF, embedded in OCT, and frozen in isopenthane precooled in liquid nitrogen. Cryostat sections (5 μm thick) were postfixed with 4% PAF, blocked with 5% goat serum (Vector Laborato-ries, Burlingame, Calif.), 1% bovine serum albumin (BSA), 0.1% Triton X-100 in PBS, and incubated with rabbit anti-GFP antibodies (Invitrogen), followed by anti-rabbit IgG-FITC-labelled secondary antibodies.

Statistical Analysis

The results are shown as mean±standard deviation (SD) as derived by unpaired Student t- test. The values are considered significantly different when $p<0.05$. All experiments were repeated three times, unless otherwise stated.

Results

Generation of the Clonal Cell Line m17.ASC

Inguinal adipose tissue, obtained from 10 week old fvb female mice, was fragmented in small pieces, digested with collagenase and after elimination of mature adipocytes and erythrocytes, Sca-1 positive (Sca-$1^{POS}$) cells were isolated by immunomagnetic procedure from the remaining stromal vascular fraction (SVF). Recovered cells were plated at a density of $1\times10^5$ cells/cm$^2$ in expansion. Adherent cells appeared as a homogeneous population highly positive for Sca-1 in immunofluorescence (FIG. 1a and c). Sca-1 expression in this cell population declined after few passages (FIG. 1b) and cells generally displayed morphological signals of senescence and stopped to proliferate after 7-9 passages. At the second passage cells were plated also at low concentrations (200 cells/cm$^2$) and a colony emerged from a single cell. This original clone was recloned and has been propagated since then for more than 20 months and was named m17.ASC. It displays the fibroblast-like morphology (FIG. 1a) typical of mesenchymal stem cells.

The m17.ASC cell-line has been deposited—under the provisions of the Budapest Treaty—with the Advanced Biotechnology Center (CBA), Interlab Cell Line Collection, Largo R. Benzi 10, Genoa 16132(Italy), with accession number ICLC PD 10001, on Nov. 10, 2010.

The m17.ASC Line Expresses Markers of Stemness

Cells were constantly analyzed for the expression of different stemness markers, namely Sca-1, c-kit, Islet 1, nestin, Oct4 and nucleostemin in semiquantitative RT-PCR (FIG. 1b) and no differences were observed at the different passages. They were constantly positive for all these markers except for the embryonal stemness marker Oct4. By contrast, cells from primary culture, which at the beginning expressed the same markers, although some (nestin and nucleostemin) at lower levels, displayed the tendency to loose their expression within few passages. The only notable exception was Islet 1, which unspectedly was expressed at high levels in the primary cultures and then decreased already after the second passage. Cytofluorimetric analysis confirmed the expression of Sca-1 and c-kit (CD117) in m17.ASC cells (FIG. 1c). Moreover these cells expressed also the mesenchymal marker CD44, CD106 at high levels, and CD34 at lower levels. They were negative for the endothelial marker CD31 and the hematopoietic markers CD45 and F4/80. L929 cells used as control do not express any of the sternness marker, except nucleostemin (Nst).

The m17.ASC Line Displays Multipotency

Figure 2:
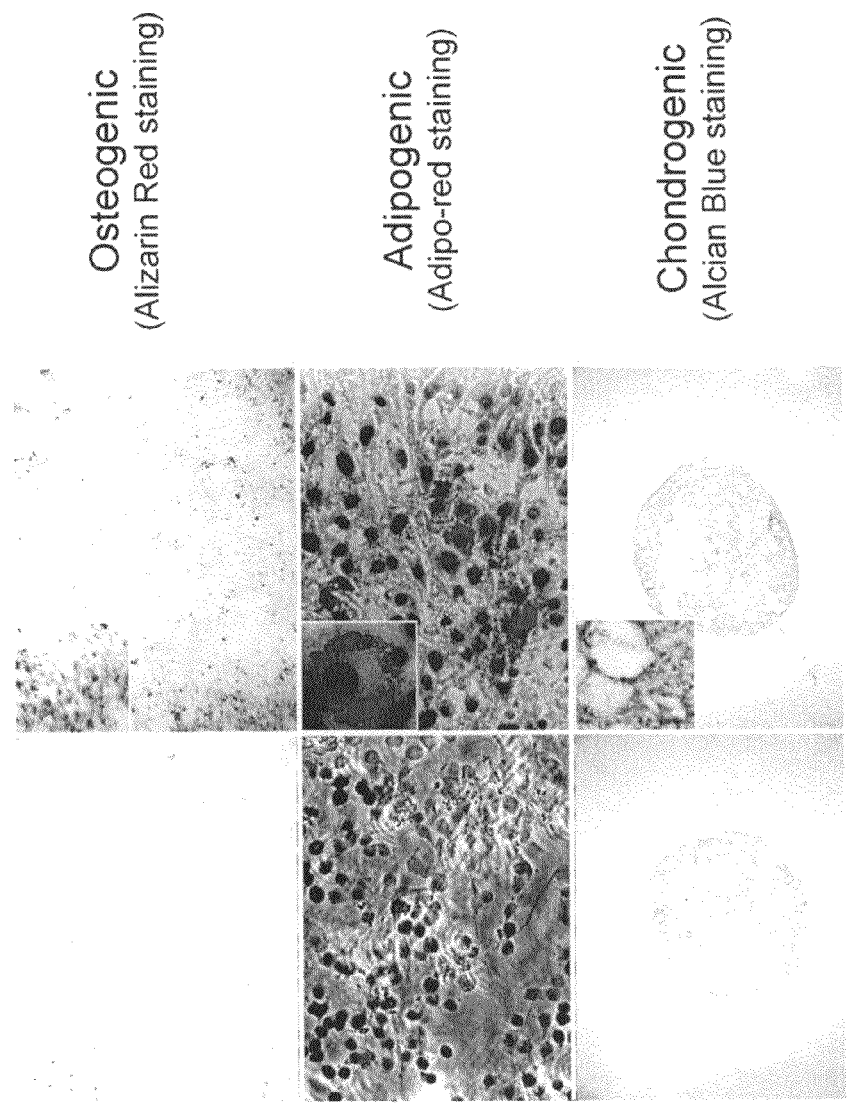
FIG. 2: The m17.ASC is multipotent. Cells were cultured in normal expansion medium (left) or in appropriate media per specific differentiation towards adipocytic, osteogenic and chondrogenic phenotypes (right). One representative experiment out of the three performed is reported.

This spontaneously immortalized cell line displayed the multilineage potential of MSC. Indeed, when cultured in appropriate differentiation media, m17.ASCs acquired features of the osteogenic, adipogenic, and chondrogenic phenotypes, as they were specifically stained with alizarin red, adipo-red and Alcian blue respectively (FIG. 2).

Karyotypic Analysis of the m17.ASC Line

Figure 3:
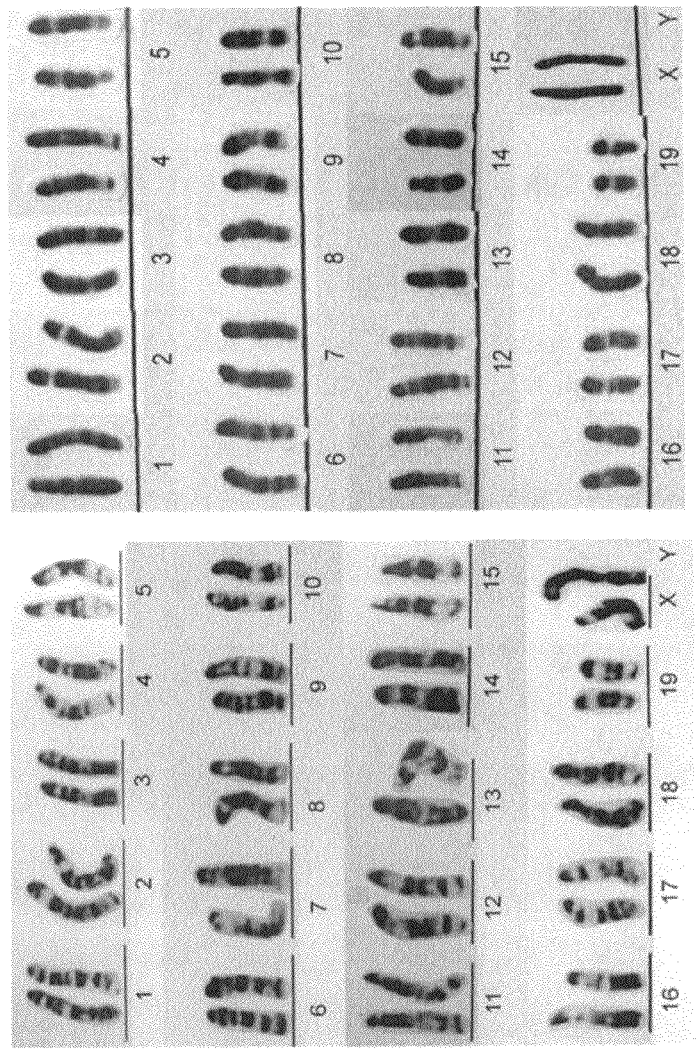
FIG. 3: Kariotypic analysis of m17.ASC. G-banding chromosome karyotype analysis of m17.1ASC cells at two passages (p10 and p73), which was normal if compared with normal mouse karyotype (19,XX). One representative experiment out of the two performed is reported.

During entire cell culture time, m17.ASC G-banding analysis did not revealed any chromosome alterations, if compared with normal mouse karyotype. Cell kariotype analysis on two different in vitro passages (p10 and p73) are shown (FIG. 3).

Telomere Dynamics

Figure 4:
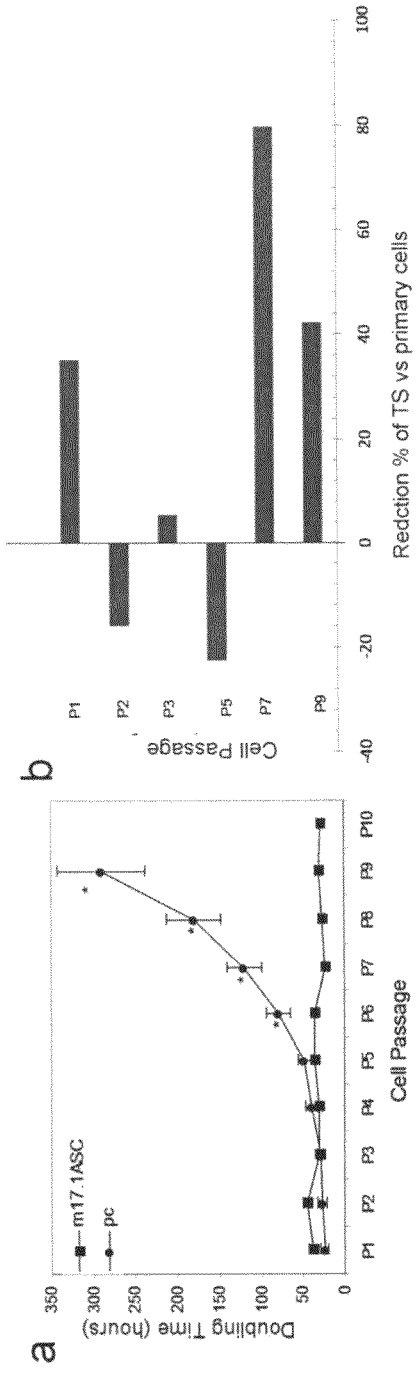
FIGS. 4a and 4b: Population doublings (PD) and telomere dynamics in m17.1.ASC line. Every three days $1 \times 10^5$/cm$^2$ of m17.1ASC and primary cells were passaged sequentially. Passage 1 (P1) and the following passages for m17.1ASC correspond to p84 and the following until p91 (FIG. 4a). Doubling time of m17.1ASC are constant and lower than those of primary SVF cells from p6 on. Telomere length was measured in the corresponding cell passages and relative data are expressed as the percent of reduction (left) or increase (right) of telomere length, measured as T/S ratio respect to the parental cell line, set as 0 value. Starting PD was 84. Time interval for each data set was 3 days (FIG. 4b). Representative experiments out of the three performed are reported. * p<0.05, Student's t test.

Telomere length was evaluated on m17.ASC from passage 83 to passage 91, and the same cultures were used to calculate the duplication time. Isolated primary stem cells were used as reference. Both the clone and the primary cultures up to the fifth passage displayed a constant doubling time of 32 hours (FIG. 4a). However, after the fifth passage the mean doubling time of primary cells was 93 hours. For each time point the percentage of reduction of telomeres length in comparison to that of the primary cells at passage 1 was evaluated. Telomeres displayed a strong erosion (more than 70%) if compared to primary cells (FIG. 4b), but they displayed a rather constant length in m17.ASC from p83 to p91. These data indicate a possible stabilization of telomeres.

Figure 5:
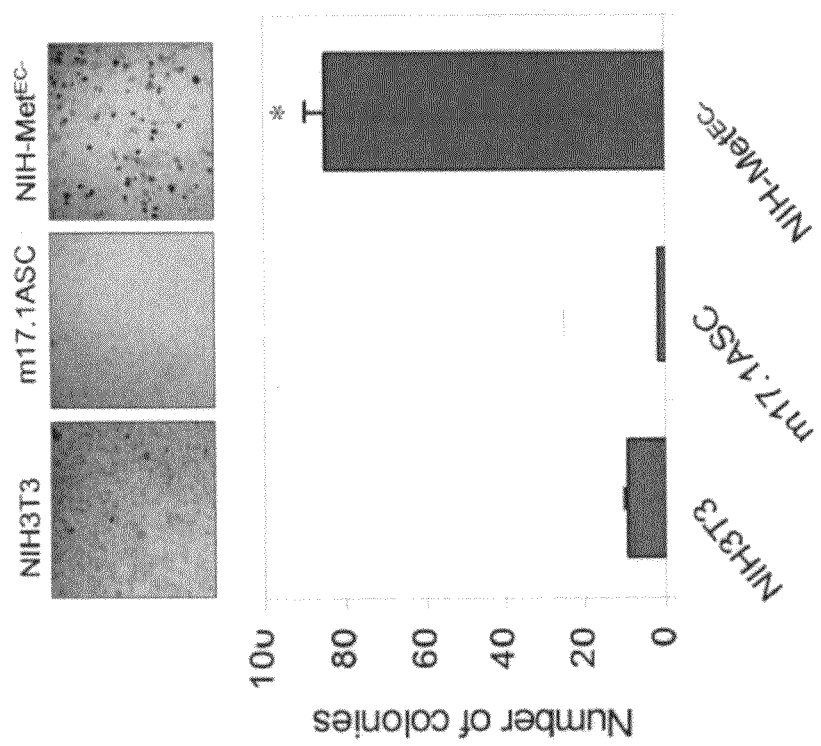
FIG. 5: The m17.ASC line maintains the properties of a normal immortalized cell line and does not show transforming properties in vitro. Transforming activity was assessed in a soft agar assay, which allows only anchorage-independent cell proliferation. In these conditions m17.ASC produced even a lower number of colonies relative to NIH-3T3 cells used as negative control. By contrast transformed NIH-3T3-Met-EC- gave a high number of colonies. Representative experiments out of the three performed are reported. * p<0.05, Student's t test.

The m17.ASC Line Maintains the Properties of a Normal Immortalized Cell Line, but does not Display a Transformed nor a Tumorigenic Phenotype Cell immortalization is often accompanied by transformation and acquisition of a tumorigenic phenotype. To evaluate this possibility, m17.ASC cells were tested for their ability to grow in anchorage-independent conditions and thus plated in soft agar. NIH-3T3-Met-EC- (a transformed and tumorigenic cell line generated in our laboratory—Merlin et al., 2009) and NIH-3T3 cells were used as positive and negative controls respectively. Cultures were monitored for 21 days: very few colonies, and in any case fewer than in the negative control of NIH-3T3 cells, could be observed at the end of the experiment in the case of m17.ASC cells, while a significant number of colonies grew up in plates seeded with NIH-3T3-Met-EC- (FIG. 5). To corroborate this in vitro finding cells were tested for their ability to form tumors in syngeneic mice, by subcutaneous injection of $5 \times 10^5$ and $2 \times 10^6$ m17.ASC cells. In none of the six animals/group a tumor developed in a period of 8 months, the time of observation reached so far. It can thus be concluded that this cell line behaves as a normal immortalized cell line and is devoid of transforming or oncogenic potential.

The m17.ASC Line can Differentiate Towards the Cardiomyogenic Phenotype

Figure 6:
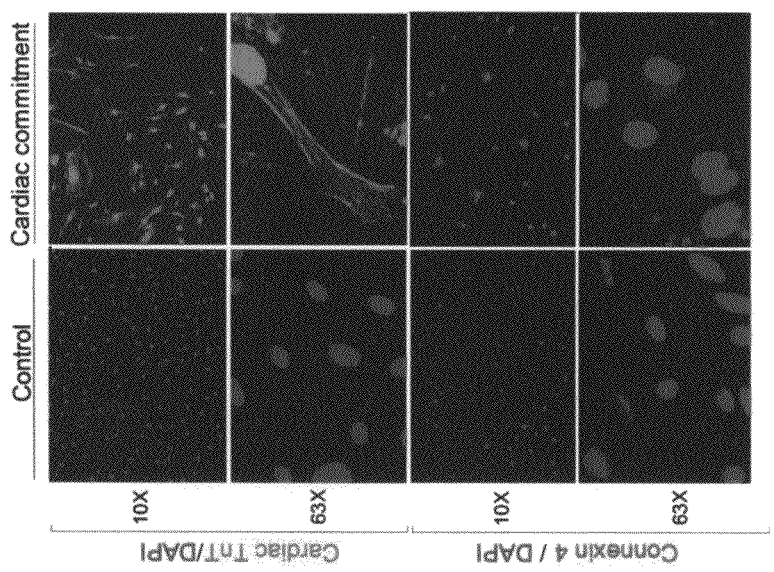
FIG. 6: The m17.ASC can be induced towards a muscle/cardiac phenotype. Cells were cultured on fibronectin-coated coverslips in an appropriate cardiac differentiation medium for 1 month, then fixed, permeabilized, and immunostained for Connexin 43 or Troponin T and examined in a fluorescentce microscope. One representative experiment out of the three performed is reported.
Figure 7:
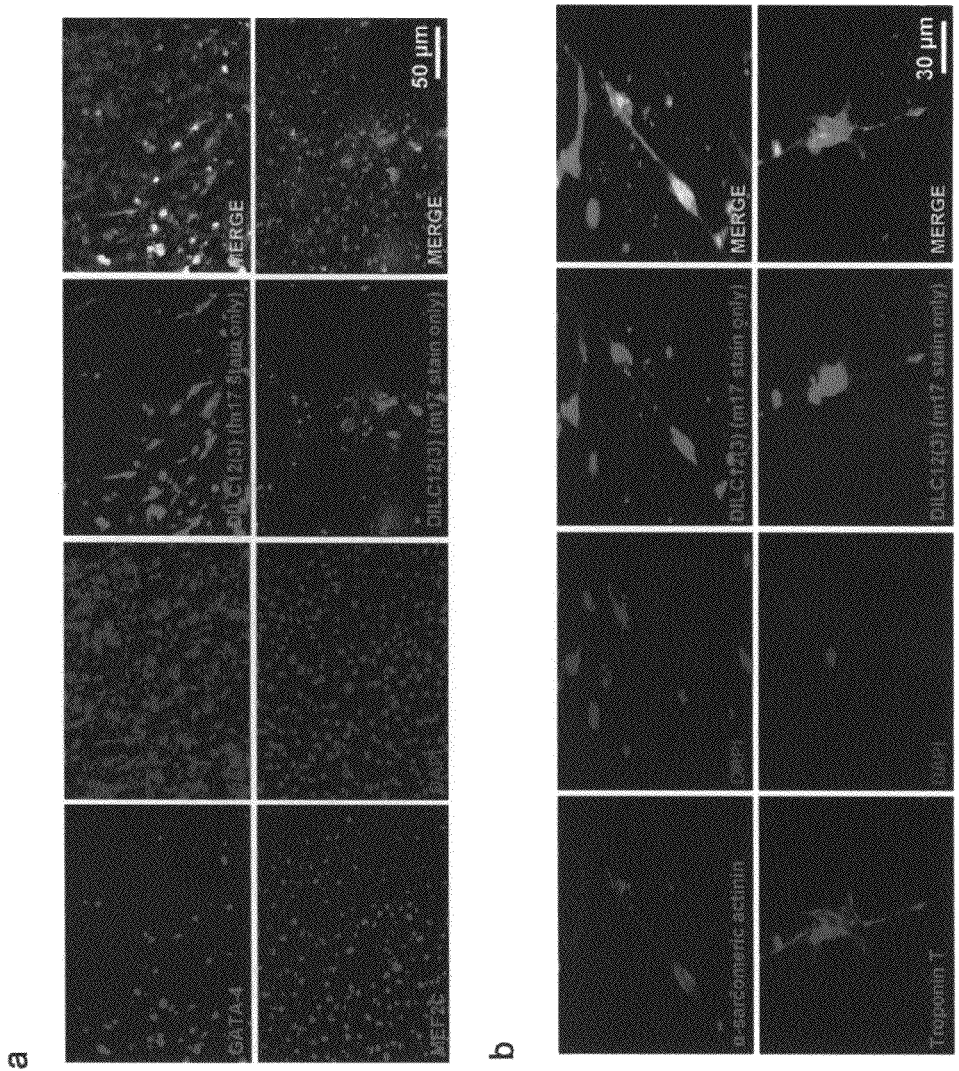
FIGS. 7a and 7b: The m17.ASC can be induced towards a muscle/cardiac phenotype, upon co-culture with neonatal cardiomyocytes. DIIC12(3)-labelled m17.ASCs (red) were co-cultured with neonatal cardiomyocytes for 7 days, then fixed, permeabilized, immunostained for GATA-4 or MEF2c (green, top and bottom panels respectively) or DAPI (blue) and examined at a fluorescence microscope, singly or after merging (FIG. 7a). DIIC12(3)-labelled m17.ASCs (red) were co-cultured, processed as above for fluorescence and immunostained for alpha-cardiac actinin or cardiac Troponin T (green, top and bottom panels respectively) or DAPI (blue) and examined at a fluorescence microscope, singly or after merging (FIG. 7b). Representative experiment out of the three performed are reported.

When cells were plated on fibronectin and maintained for 1 month following a protocol for muscle/cardiac differentiation, cells acquired the expression of two markers of muscle/cardiac differentiation, namely, connexin 43 and troponin T (FIG. 6). When co-cultured on neonatal cardiomyocytes for 7 days a significant percentage of the DIIC12(3)-labelled m17.ASCs cells acquired the expression of GATA-4 and MEF2c, as detected in immunofluorescence, while when cultured alone, the same cells were positive only in <1% (FIG. 7a, Table 2). Also adherent cells from the stromal vascular fraction of adipose tissue, from which the m17.ASC clone was derived, became positive for the expression of GATA-4 and MEF2c, when co-cultured with neonatal cardiomyocytes (Table 2). In the same kind of experiment few co-cultured DILC12(3)-labelled m17.ASCs acquired the expression of alpha-sarcomeric actin and troponin T (FIG. 7b). All together these results indicate that m17.ASC can differentiate towards the cardiomyogenic phenotype and behave in this respect, in the same manner as the bulk population from which they were derived.

TABLE 2

Expression of cardiac markers upon co-culture on neonatal CPC

| Cells | Positive/DIIC12(3)-labelled (cell %)* | |
|---|---|---|
|  | GATA-4 | MEF2c |
| m17.ASC + nCPC | 14.96 ± 0.9§ | 15.85 ± 0.7§ |
| m17.ASC | 0.6 ± 0.2 | 0 |
| SFV + nCPC | 18 ± 1.2§ | 15.1 ± 0.8§ |
| SFV | 0 | 0 |

Figure 8:
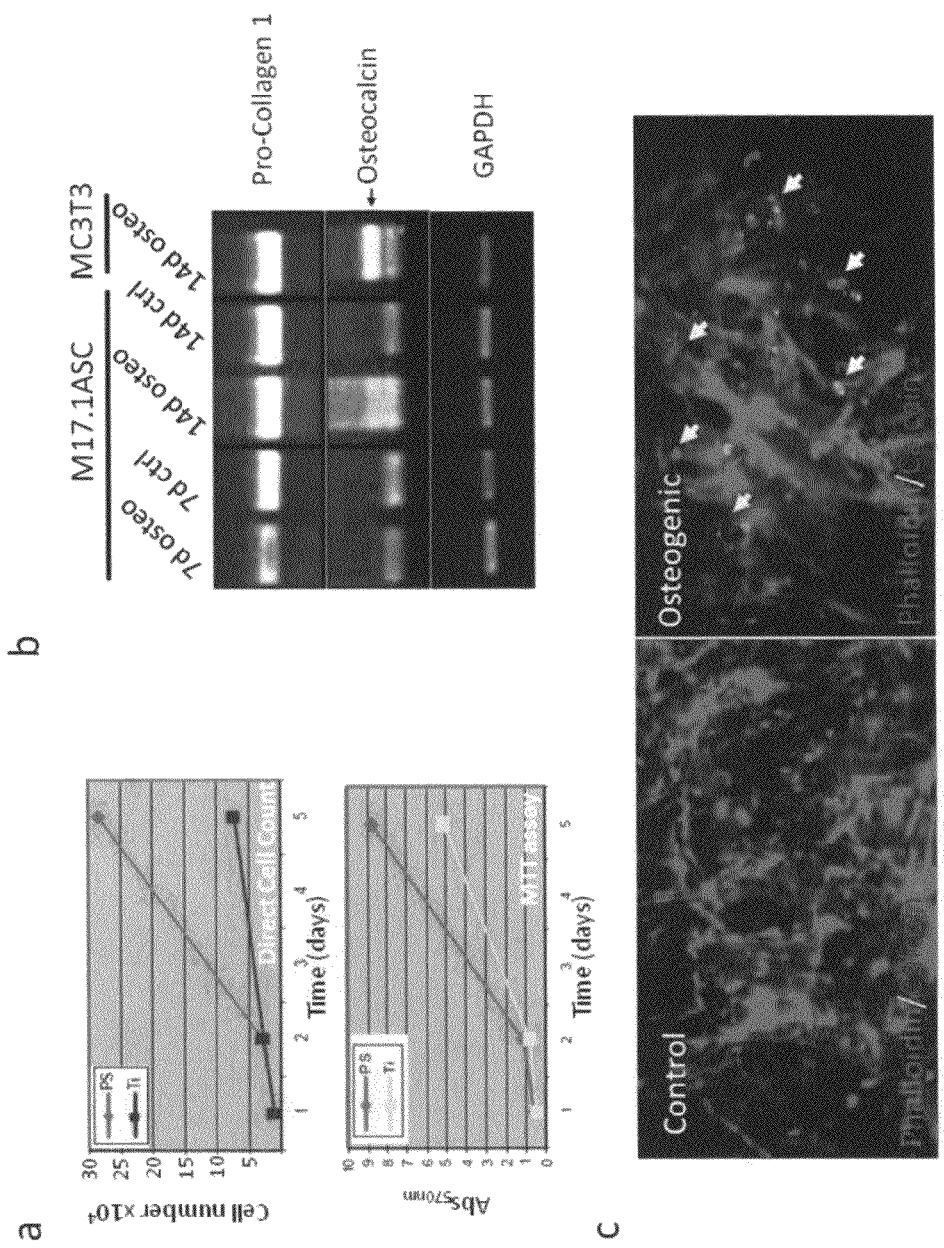
FIGS. 8a-8c: The m17.ASC line proliferates and can be induced towards osteogenic differentiation on titanium matrices. Cells were seeded on titanium grade disks and their proliferation and viability was assessed by direct cell counting, after detachment form substrate (left) or in a MTT assay (right) in sequential days (FIG. 8a). (PS=polystyrene, Ti titanium). Cells on titanium disks were incubated in the osteoinducing medium for 7 or 14 days, with two medium changes every week; then mRNA was extracted, retrotranscribed and RT-PCR for osteogenic markers were carried on, equalizing on the basis of an RT-PCR for GAPDH (FIG. 8b). Samples induced to differentiation for days were fixed and stained with calcein-FITC and phalloidin-TRITC, which detect extracellular calcium deposits (white arrows) and cell cytoskeleton respectively (FIG. 8c). Representative experiments out of the three performed are reported.

*At least 500 DIIC12(3)-labelled cells were counted in each of the three experiments performed.
§$p < 0.05$, Student's t test The m17.ASC Line can be Induced to Produce Bone Prototissues, When Plated on Titanium Matrices m17.ASCs ($8 \times 10^3$) were seeded onto Titanium grade 2 scaffolds and their adhesion, proliferation and osteogenic differentiation potential on this scaffold analyzed and compared to those of the same cells plated in conventional polystyrene culture plates. On titanium scaffolds cells were able to adhere and proliferate, although at a lower grade, as shown both on the basis of direct cell counting and in a MTT assay (FIG. 8a). When induced to osteogenic differentiation, they expressed the early osteogenic marker osteocalcin, beside the more ubiquitous pro-collagen 1, both of which were detected by RT-PCR (FIG. 8b). Moreover, osteogenic differentiation of m17.ASC on titanium scaffolds was confirmed by the presence of extracellular calcium deposits, detectable by calcein staining (late marker) (FIG. 8c). The osteoblastic cell line MC3T3 was used as positive control in these experiments.

The m17.ASC Line can Engraft in Syngeneic Mice

Figure 9:
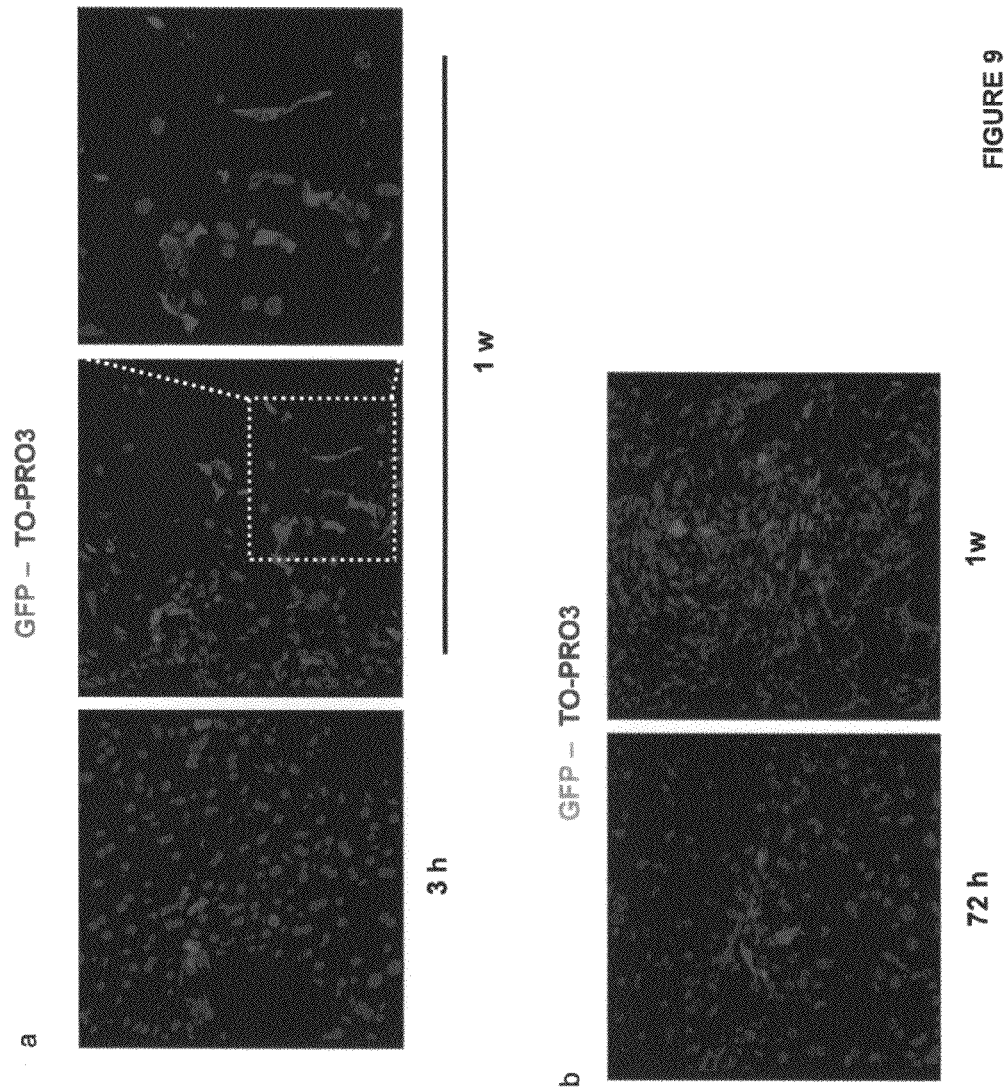
FIGS. 9a and 9b: The m17.ASC line engrafts in syngeneic mice. Liver sections from mice killed after different periods of time upon GFP-m17.ASC transplantation by intraportal (FIG. 9a) and intrasplenic (FIG. 9b) injection were stained with GFP antibody (green) and To-pro-3 (blue) and analyzed by confocal microscopy. Cell engraftment was detected 3 h and 1 week after transplantation in (FIG. 9a) and after 72 h and 1 week in (FIG. 9b). Original magnification is 630×, except in the final enlagement of the boxed area, that is 1200×. One representative experiment out of 3 performed is presented (3 animals per group per experiment).

Mice (fvb strain) were transplanted with GFP-m17.ASC either through intraportal vein injection or in the spleen. At different time points animals were killed, their livers excised, fixed, and sections were processed for immunofluorescent staining with anti-GFP antibodies. Labelled transplanted cells could be visualized in specimen prepared at time point 3 h as well as after 1 week in the liver in both cell transplantation protocols (FIG. 9a, b).

REFERENCES

Asahara T Murohara T, Sullivan A, Silver M, van der Zee R, Li T, Witzenbichler B, Schatteman G, Isner J M. Isolation of putative progenitor endothelial cells for angiogenesis. Science 1997; 275: 964-967

Burdick J A, Vunjak-Novakovic G. Review: Engineered Microenvironments for Controlled Stem Cell Differentiation. Tissue Eng Part A 2009; 15: 205-219.

Callicott R J, Womack J E. Real-time PCR assay for measurement of mouse telomeres. Comparative Medicine 2006; 56:17-22.

Cawthon, R M. Telomere measurement by quantitative PCR. Nucleic Acids Res 2002; 30:e47. 1-6.

Festi H, Hoareau L, Bes-Houtmann S, Péquin A M, Gonthier M P, Munstun A, Hoarau J J, Césari M, Roche R. et al., Surface protein expression between human adipose tissue-derived stromal cells and mature adipocytes. Histochem. Cell Biol. 2005; 124:113-121

Follenzi A, Benten D, Novikoff P, Faulkner L, Raut S, Gupta S. Transplanted endothelial cells repopulate the liver endothelium and correct the phenotype of hemophilia A mice. J Clin Invest. 2008; 118:935-45.

Forte G, Minieri M, Cossa P, Antenucci D, Sala M, Gnocchi V, Fiaccavento R, Carotenuto F, De Vito P, Baldini P M, Prat M, Di Nardo P. Hepatocyte growth factor effects on mesenchymal stem cells: proliferation, migration, and differentiation. Stem Cells. 2006 January;24(1):23-33

Fraser J K, Wulur I, Alfonso Z, Hedrick M. Fat tissue: an underappreciated source of stem cells for biotechnology. Trends in Biotechnology 2006; 24: 150-154.

Gronthos S, Franklin D M, Leddy H A, Robey P G, Storms R W, Gimble J M. Surface protein characterization of human adipose tissue-derived stromal cells. J. Cell. Physiol. 2001; 189:54-63.

Kern S, Eichler H, Stoeve J, Klüter H, Bieback K. Comparative Analysis of Mesenchymal Stem Cells from Bone Marrow, Umbilical Cord Blood, or Adipose Tissue. Stem Cells 2007; 24: 1294-1301.

Lee J W, Kim Y H, Kim S H, Han S H, Hahn S B. Chondrogenic differentiation of mesenchymal stem cells and its clinical applicatins. Yonsei Med J 2004; 30:45 Suppl: 41-7.

Merlin S, Pietronave S, Locarno D, Valente G, Follenzi A, Prat M. Deletion of the ectodomain unleashes the transforming, invasive, and tumorigenic potential of the MET oncogene. Cancer Sci. 2009; 100:633-638.

Mitelman F. ISCN 1995. An International System for Human Cytogenetic Nomenclature. Basel: Karger; 1995. Available from: http://www.iscn1995.org/. Accessed in 2007 (June 4).

Pagliari S, Vilela-Silva A C, Forte G, Pagliari F, Mandoli C, Vozzi G, Pietronave S, Prat M, Licoccia S, Ahluwalia A, Traversa E, Minieri M, Di Nardo P. Cooperation of Biological and Mechanical Signals in Cardiac Progenitor Cell Differentiation. Adv Mater. 2010 Nov 12. [Epub ahead of print].

Seabright M. A rapid banding technique for human chromosomes. Lancet. 1971; 2:971-2.

Yamakawa K, Iwasaki H, Masuda I, Ohjimi Y, Honda I, Saeki K, Zhang J, Shono E, Naito M, Kikuchi M. The utility of alizarin red s staining in calcium pyrophosphate dihydrate crystal deposition disease. J Rheumatol. 2003; 30:1032-5.

The invention claimed is:

1. A spontaneously immortalized multipotent mesenchymal cell-line which is m17.ASC (Accession No. ICLC PD No. 10001), wherein said cell-line has been isolated from mouse subcutaneous adipose tissue, and wherein said cell-line presents fibroblastoid morphology and expresses Sca-1, c-Kit/CD117, nestin, nucleostemin, CD44 and CD106 markers.

2. The spontaneously immortalized multipotent mesenchymal cell-line according to claim 1, wherein said cell-line does not express CD31, CD45 and F4/80 markers.

3. The spontaneously immortalized multipotent mesenchymal cell-line according to claim 1, wherein said cell-line does not have in vitro transforming activity.

4. The spontaneously immortalized multipotent mesenchymal cell-line according to claim 1, wherein said cell-line does not have in vivo tumorigenic activity.

5. The spontaneously immortalized multipotent mesenchymal cell-line according to claim 1, wherein said cell-line maintains a stable proliferative ability.

6. The spontaneously immortalized multipotent mesenchymal cell-line according to claim 1, wherein said cell-line is further transduced with GFP.

7. The spontaneously immortalized multipotent mesenchymal cell-line according to claim 1, wherein said cell-line is capable of acquiring at least one phenotype selected from the group consisting of: adipogenic, chondrogenic, osteogenic, tenocytes, endothelium, hepatocytic, skeletal muscle, smooth muscle, cardiogenic, paradontal ligament, tooth pulp, and dentin, when cultured in a culture medium containing at least one specific phenotype differentiation factor or molecule.

* * * * *